United States Patent
Holm et al.

(10) Patent No.: US 10,545,076 B2
(45) Date of Patent: Jan. 28, 2020

(54) DETERMINATION OF ANALYTES IN A SAMPLE MATRIX BY SOLVENT EXTRACTION

(71) Applicant: Foss Analytical A/S, Hilleroed (DK)

(72) Inventors: Claus Holm, Hilleroed (DK); Malin Dahl, Hilleroed (DK); Christer Zoffmann Bisgaard, Hilleroed (DK)

(73) Assignee: Foss Analytical A/S, Hilleroed (DK)

( * ) Notice: Subject to any disclaimer, the term of this patent is extended or adjusted under 35 U.S.C. 154(b) by 272 days.

(21) Appl. No.: 15/515,794

(22) PCT Filed: Oct. 20, 2014

(86) PCT No.: PCT/IB2014/065461
§ 371 (c)(1),
(2) Date: Mar. 30, 2017

(87) PCT Pub. No.: WO2016/063104
PCT Pub. Date: Apr. 28, 2016

(65) Prior Publication Data
US 2017/0248500 A1  Aug. 31, 2017

(51) Int. Cl.
G01N 1/40 (2006.01)
B01D 11/02 (2006.01)
G01N 1/34 (2006.01)
G01N 30/60 (2006.01)
G01N 30/06 (2006.01)

(52) U.S. Cl.
CPC .......... *G01N 1/40* (2013.01); *B01D 11/0203* (2013.01); *G01N 1/34* (2013.01); *G01N 30/60* (2013.01); *G01N 2001/4061* (2013.01); *G01N 2030/062* (2013.01)

(58) Field of Classification Search
None
See application file for complete search history.

(56) References Cited

FOREIGN PATENT DOCUMENTS

WO  WO-2011/023230 A1  3/2011

OTHER PUBLICATIONS

Ho et al. Analyst, 2002, 127, 608-613.*
Górecki et al. Analyst, 1999, 124, 643-649.*
Vignali et al Journal of Immunological Methods 243 (2000) 243-255.*
A. Rahmani et al: "Qualitative and Quantitative Analysis of Mycotoxins", Comprehensive Reviews in Food Science and Food Safety, vol. 8, No. 3, Jul. 1, 2009 (Jul. 1, 2009), pp. 202-251, XP055195137, ISSN: 1541-4337, DOI: 10.1111/j.1541-4337.2009.00079.x.
Pittet Alain: "Modern methods and trends in mycotoxin analysis", Mitteilungen Aus Lebensmitteluntersuchung Und Hygiene, Bundesamt Fuer Gesundheit, Bern, CH, vol. 96, No. 6, Jan. 1, 2005 (Jan. 1, 2005), pp. 424-444, XP009091399, ISSN: 1424-1307.
Zabe: "Ethanol Extraction Method for a Rapid Test for Aflatoxin in Corn", Sep. 14, 2006, ACS Symposium Series 1001, pp. 297-305, XP008125177.
Mulders Ed J et al: "Gas chromatographic determination of deoxynivalenol in cereals", Zeitschrift Fuer Lebensmittel-Untersuchung Und -Forschung. A,European Food Research and Technology, Springer, Heidelberg, DE, vol. 183, No. 6, Dec. 1, 1986 (Dec. 1, 1986), pp. 406-409, XP002595889, ISSN: 1431-4630.
European Union Commission Regulation (EC) No. 401/2006, Feb. 23, 2006 (Feb. 23, 2006).
International Search Report PCT/ISA/210 for International Application No. PCT/IB2014/065461 dated Jun. 23, 2015.
Written Opinion of the International Searching Authority PCT/ISA/237 for International Application No. PCT/IB2014/065461 dated Jun. 23, 2015.
Evelyne Nguegwouo et al., "An Overview of some Major Mycotoxins in Food and their Detection Methods", Nutrition and Food Toxicology, 3.1 (2019): 564-576.

* cited by examiner

*Primary Examiner* — Michael L Borin
(74) *Attorney, Agent, or Firm* — Harness, Dickey & Pierce, P.L.C.

(57) ABSTRACT

Determination of Analytes in a Sample Matrix by Solvent Extraction A method for the assay of one or more analytes in a sample matrix comprising the steps of: performing analyte extraction on the sample matrix, said analyte extraction comprising combining the sample matrix with a solvent for an extraction period which is less than that required for reaching equilibrium; and separating the analyte containing solvent from the sample matrix; next measuring a level of analyte present in the separated solvent; and then applying in a computer a calibration by which is established a mathematical relationship between levels of analyte extracted from each of a plurality of reference samples by means of the process employed above in the extraction for the sample matrix and a reference value of the levels of analyte for each reference sample to thereby derive a measure of the level of analyte in the sample matrix. Specifically a method to determine the amount of mycotoxins in cereal grain, especially OTA (ochratoxin A) and DON (deoxynivalenol) by mixing with a solvent comprising water alcohol mixture, with 20-40% ethanol by volume.

14 Claims, 8 Drawing Sheets

DETERMINATION OF ANALYTES IN A SAMPLE MATRIX BY SOLVENT EXTRACTION

The present invention relates to a method for the determination of analytes in a sample matrix, particularly of mycotoxin levels in cereal grains, and in particular to a method involving analyte extraction using solvents.

Mycotoxins tend to be very stable and may produce severe illness when ingested, inhaled, or introduced into the body by any other means. For instance, mycotoxins are known to be poisonous or carcinogenic when consumed by humans or animals. Mycotoxins are produced by molds and fungi during their growth on food and feed and may remain in food and feed long after the mold or fungus that produced them has died. Therefore products that are not visibly moldy or do not test positive for mold count can still contain potentially dangerous levels of mycotoxins.

Several countries have currently established or proposed regulations for control of mycotoxins (primarily the aflatoxins) in food and animal feed. In order to harmonize these regulations, the Food and Drug Administration, for example, has established guidelines for the levels of aflatoxin permitted in commodities for further processing. The permitted levels vary depending upon the intended end usage of the commodity. The European Union, for example, has also established regulations for the levels of ochratoxin A (OTA), Deoxynivalenol (DON); Zearalenone (ZEA) and several other mycotoxins.

The enforcement of these regulations requires accurate monitoring of suspected commodities. However, since mycotoxins tend to be inhomogeneously distributed throughout a lot of cereal it becomes prohibitively expensive to carry out laboratory analysis on the number of samples required to be representative of the particular lot. Therefore, there is a continuous need for a rapid and inexpensive method for detecting the presence of mycotoxins in a lot of cereal grain so that, a lot containing mycotoxins may be rapidly identified to allow further, more accurate analysis to be performed in a laboratory.

Solvent extraction is a vital step in most detection methodologies. Indeed many authorities do not prescribe specific determination method requirements; rather certain performance criteria are mandated: for example, with the European Union Commission Regulation (EC) No 401/2006 of 23 Feb. 2006 criteria are prescribed which include extraction efficiency requirements stipulating a recovery of between 50% and 120% depending on mycotoxin. Generally, these requirements are selected in order to ensure that any test methodology will achieve acceptable levels of precision, accuracy and levels of detection. If extraction is unable to be performed reliably and consistently then the results from the analysis will be imprecise. It is therefore generally accepted that extraction should be performed for a period long enough to reach equilibrium for the extraction process; in the case of reference methods for mycotoxin analysis this period is of the order of an hour. Obviously, this adds considerably to the overall analysis time and leads away from the provision of a rapid assay methodology.

However, it is known from Zabe et. al ('Ethanol Extraction Method for a Rapid Test for Aflatoxin in Corn', pages 297-305, ACS Symposium Series 1001—Food Contaminants—Mycotoxins and Food Allergens) to provide a method which includes the rapid solvent extraction of a mycotoxin. Here it is disclosed that using a mixture by volume of 80% ethanol and 20% water sufficient extraction of aflatoxin from corn to meet regulatory demands may be achieved in one minute. Unfortunately, this level of ethanol represents a small but still unacceptable fire risk as well as providing a solvent solution that is hazardous both to health and to the environment.

Another extraction methodology is described in WO 2011/023230 of FOSS Analytical AB. Here it disclosed that adequate extraction of mycotoxin from cereal grain may be achieved using a solvent mixture by volume of 20% ethanol and 80% water. This significantly reduces the risk and hazard aspects associated with the higher concentration ethanol or other organic solvents (such as methanol or acetonitrile) but unfortunately adequate extraction takes around one hour to achieve, which does not lend itself to utilisation in a rapid determination technique.

It is the aim of the present invention to alleviate at least one of the problems associated with the known extraction techniques.

According to one aspect of the present invention there is provided a method for the quantitative assay of one or more analytes, particularly mycotoxins, extracted from a sample matrix, particularly cereal grain, comprising the steps, not essentially in the order presented, of: A) performing analyte extraction on a plurality of reference sample matrices, each having a different reference value level of analyte, said analyte extraction comprising combining each sample matrix with a solvent for a same extraction period which is less than a time required for reaching equilibrium; and separating the analyte containing solvent from the sample matrix; B) measuring a level of analyte present in the separated solvent obtained from each reference sample matrix; C) generating a computer executable calibration by which is established a mathematical relationship between levels of analyte extracted from each of the reference matrices and the reference level of analyte in the same each reference matrix; D) repeating the steps A and B substituting a sample matrix having an unknown level of analyte for the reference sample matrix to obtain a measure of a level of analyte in the separated solvent for the sample matrix; and E) applying in a computer the calibration generated at step C to the level of analyte determined at step D to thereby derive a measure of the level of analyte in the sample matrix. With the realisation that reliable and repeatable incomplete, non-equilibrium extraction under reproducible extraction conditions may be associated with the level of analyte present in the sample matrix which would be obtained from an equilibrium extraction the inventors have provided an assay method that does not rely on reaching extraction equilibrium. This allows an assay to be performed in shorter times and/or with solvents not normally considered suitable.

In order to achieve a rapid separation and thereby enhance the reliability and repeatability of the extraction process the separation may be usefully performed by applying a force to separate the solid and liquid materials. This may be done by forcing the solvent/matrix mixture through a filter, such as may simply and reliably be achieved using a French press, or by using a centrifuge typically of either the sediment or of the filter type.

It will be appreciated that it is entirely likely that one person (legal or real) may perform the steps up to and including generating the calibration model (steps A to C above) and another person (legal or real) may perform extraction and level measurements on sample matrices having an unknown level of analyte and apply the calibration model to these measurements. Thus according to another aspect of the present invention there is provided a method for the assay of one or more analytes in a sample matrix comprising the steps of performing analyte extraction on the sample matrix, said analyte extraction comprising combining the sample matrix with a solvent for an extraction period which is less than a time required for reaching equilibrium and separating the analyte containing solvent from the sample matrix; measuring a level of analyte present in the separated solvent; and applying in a computer a calibration by which is established a mathematical relationship between levels of analyte extracted from each of a plurality of reference samples by means of the process employed above in the extraction for the sample matrix and a reference value of the levels of analyte for each reference sample to thereby derive a measure of the level of analyte in the sample matrix.

These, as well as additional objects, features and advantages of the present invention, will be better understood through the following illustrative and non-limiting detailed description of embodiments of the present invention, made with reference to the drawings of the appended figures, of which:

Figure 1:
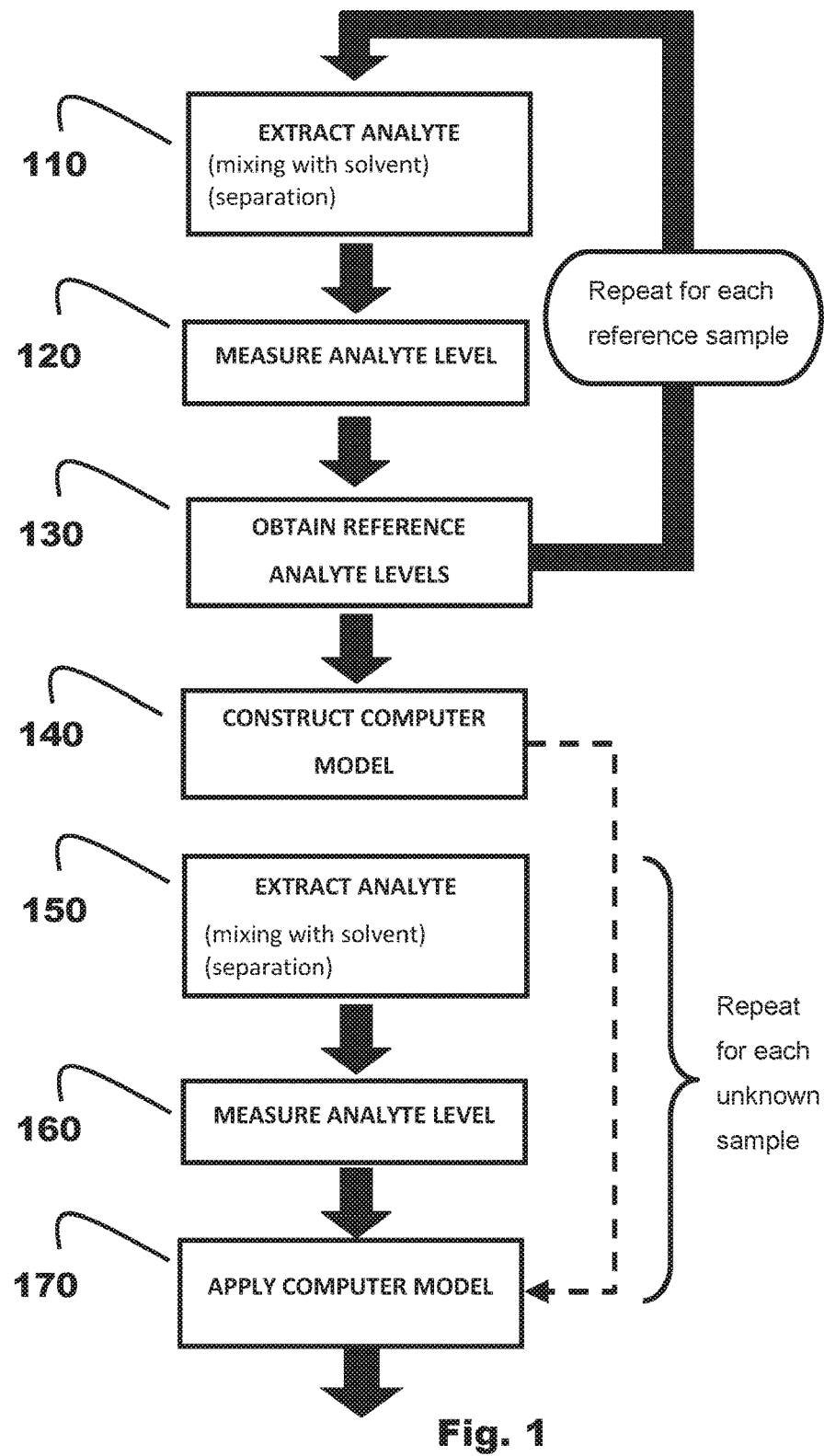
FIG. 1 shows a flow diagram illustrating an embodiment of the method according to the present invention.

An exemplary method for assay of analytes according to the present invention is illustrated generally by the flow diagram of FIG. 1. At step 110 analyte extraction is performed. This involves mixing a sample matrix with a solvent, possibly including shaking or other agitation to ensure a good mix, followed by separating the sample matrix from the solvent after an extraction period which is shorter than that necessary for reaching equilibrium but during which period analyte to be extracted from the matrix moves into the solvent in a measureable quantity.

Once separated, at step 120 the level of analyte in the solvent is measured. The measurement technique employed in this determination will of course depend on the analytes under investigation. Steps 110 and 120 will be repeated for each of a plurality of reference sample matrices having a different reference analyte level and the results for each sample matrix made available to a computer. Reference values of the level of analyte contained in each reference matrix are obtained (step 130) and also made available to the computer. These reference values could be obtained from knowledge of a level of analyte deliberately introduced into the reference matrices or from a reference measurement made on the matrices. In the latter case it is advantageous if the same measurement technique is used as that used to obtain the level of analyte in the solvent. At step 140 a computer executable mathematical model is constructed from the reference level values (reference dataset) and from those measured in the separated solvent (solvent dataset) for the same sample matrix which links an amount of analyte measured in a solvent to a level of analyte present in the sample matrix. Regression analysis of the datasets is used to model the relationship between the variables in a known manner. In particular simple linear regression may be performed on the datasets in order to determine the mathematical relationship to be expressed in the computer executable calibration model. This model is then made available to the same or a different computer for use therein in determining a level of analyte in a test sample matrix.

At step 150 an analyte extraction is performed using a test sample matrix having an unknown level of analyte. The extraction procedure employed at this step 150 is necessarily substantially similar to the one employed at step 110 to extract analyte from reference sample matrices. It is to be understood that 'substantially' is to be taken to include an extraction procedure that varies from the one employed at step 110 to an extent that does not measurably impact the amount of analyte extracted into the solvent from a same reference matrix. Once separated a measurement is made (step 160) of a level of analyte present in the separated solvent is made using a substantially similar measurement technique and process as employed to measure the level of analyte extracted from the sample matrices at step 120. This measured level is provided to the computer that has been provided with access to the computer executable calibration model and at step 170 the calibration is applied by the computer to the measured level and a quantitative determination is made of the amount of analyte present in the unknown sample matrix which may be then output from the computer in machine or preferably human understandable format.

It will be appreciated that the process steps described above need not necessarily be performed in the order provided in respect of this particular embodiment and that not all process steps needs be performed by the same person or with the same frequency to fall within the scope of the invention as claimed. Indeed it is entirely likely that one person (legal or real) may perform the steps up to and including generating the calibration model (steps 110 to 140) and another person (legal or real) may perform extraction and level measurements on sample matrices having an unknown level of analyte and apply the calibration model to these measurements (steps 150 to 170).

Typically the steps involved in the assay of unknown samples (steps 150 to 170) may be performed a large plurality of times whereas the steps involved in generating the calibration model (steps 110 to 140) may be performed relatively seldom. Thus, according to another exemplary method for the assay of one or more analytes in a sample matrix the steps to be performed comprises performing analyte extraction on the sample matrix 150, said analyte extraction comprising combining the sample matrix with a solvent for an extraction period which is less than that required for reaching equilibrium and separating the analyte containing solvent from the sample matrix; measuring a level of analyte present in the separated solvent (step 160); and, at step 170, applying in a computer a calibration by which is established a mathematical relationship between levels of analyte extracted from each of a plurality of reference samples by means of the process employed above in the extraction for the sample matrix and a reference value of the levels of analyte for each reference sample to thereby derive a measure of the level of analyte in the sample matrix.

Figure 7:
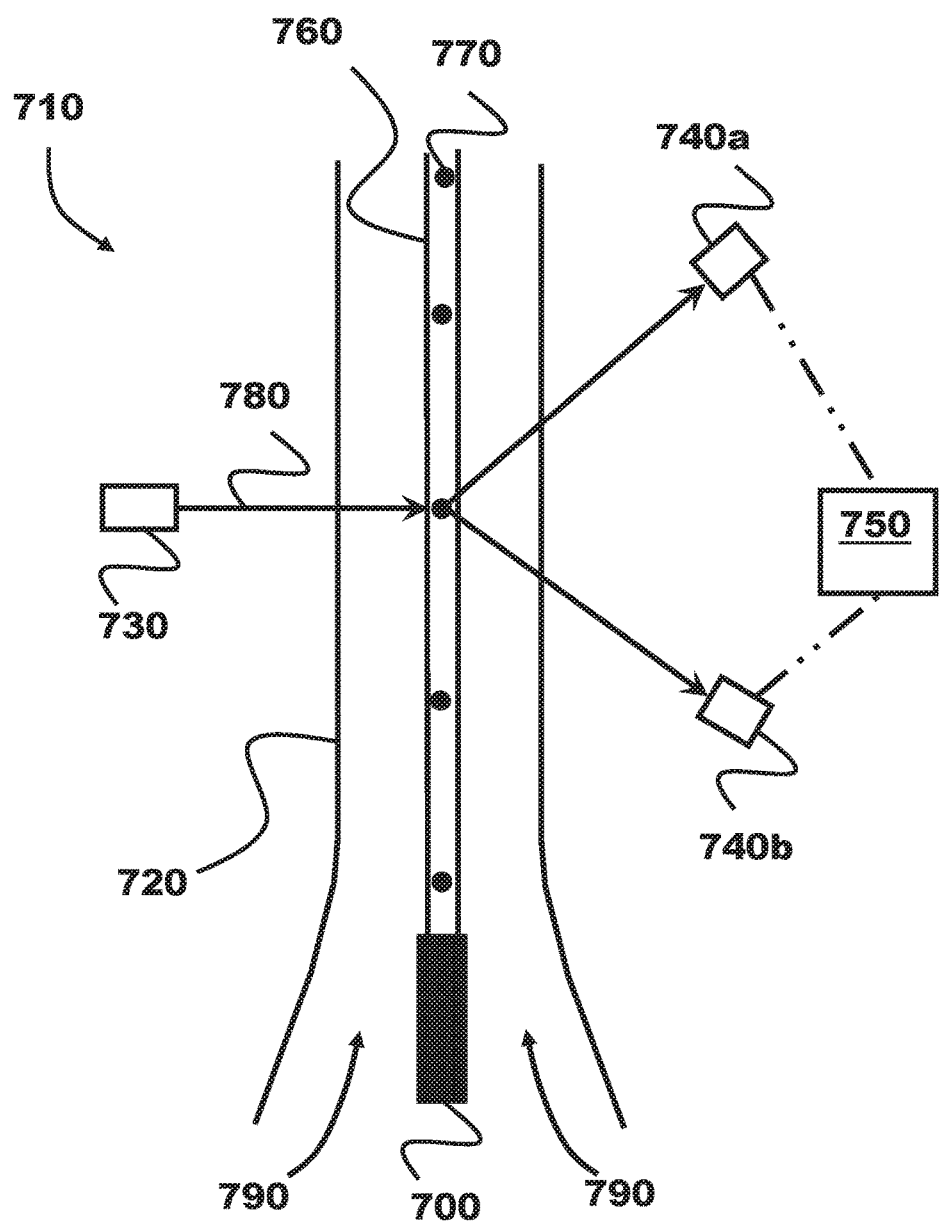
FIG. 7 shows schematically a flow cytometer arrangement suitable for measuring the level of analyte in the method according to the present invention.

Measurement of the level of analyte at step 160 (in one embodiment also at step 120) may advantageously be performed using a conventional flow cytometer arrangement 710 illustrated in FIG. 7 employing micro-beads 770 which have at their surfaces molecules with a preferential binding affinity for target analytes in the separated solvent. Such molecules may be antibodies, aptamers, molecular imprinted polymers or any known molecule having a preferential binding affinity for a one of the analytes the level of which is to be assayed. The arrangement 710 of the present exemplary embodiment comprises a flow cell 720; a light source 730; one or more optical detectors (here two, 740a, b); and a signal processor 750 operably connected to receive the outputs of the detectors 740a,b.

The separated solvent obtained at step 150 is mixed with a known amount of fluorescently labelled analyte molecules and the coated micro-beads 770. The analyte from the separated solvent and the fluorescently labelled analyte molecules compete for the available binding site on the micro-beads and once equilibrium has been reached the fluorescence from the beads will reflect their relative concentration. Traditionally, this reaction is allowed to equilibrate by utilizing 30-60 minutes incubation of the reagents but the inventors have discovered that quantitative information may be extracted after few minutes of incubation, albeit with increased uncertainty. The robustness of predictions based on early measurements may be increased by tracking the reaction kinetics, rather than measuring in a fixed time window.

A solution containing the incubated reagents is injected into the flow cell 720 through sample inlet port 700 and is surrounded by a particle free sheath liquid 790. The solution is flowed through the flow cell 720 as a hydrodynamically focused sample stream 760 within which are suspended the micro-beads 770. A light beam 780 of substantially monochromatic light is generated by the light source 730, for example a laser light source or a light emitting diode, and is made incident upon the focussed sample stream 760 in the flow cell 720. By focusing the light beam to a small spot, individual beads may be optically addressed and the fluorescence from the labelled analytes on the beads can be distinguished from that from the labelled analytes in solution. A part of the emitted light is collected, for example with a lens, filtered to select a specific wavelength range and directed towards the appropriate one or more optical detectors 740. The output from each of the optical detector 740 is sent to a signal processor 750, configured such that, for instance, the total and/or maximum fluorescence from the individual beads may be read out and stored for later analysis.

In a modification to the flow cytometer measurement arrangement 710 described above the micro-beads 770 may comprise different sets of micro-beads with each set consisting of micro-beads coated with molecules having a binding affinity for an analyte that is specific for that set and different to the other sets. The fluorescent label attached to the analyte molecule may also be selected so as to provide a different wavelength (which term includes a narrow band of wavelengths) fluorescence signal for each type of analyte. In this way multiple analytes may be readily assayed simultaneously by differentiating between the wavelengths of fluorescence detected by the detector(s) 740. As is well known, this may be achieved by using a plurality of detectors where each of the plurality is configured (for example by the addition of an appropriate filter before each detector) to detect a different fluorescence wavelength. Alternatively, the same fluorescent label is attached to the different analytes. The micro-beads 770 are then stained with a dye emitting in a different wavelength band and the intensity of the bead fluorescence is used as a label to indicate the type of analyte that this bead binds. Either method advantageously permits simultaneous detection of multiple analytes from the sample matrix.

Figure 8:
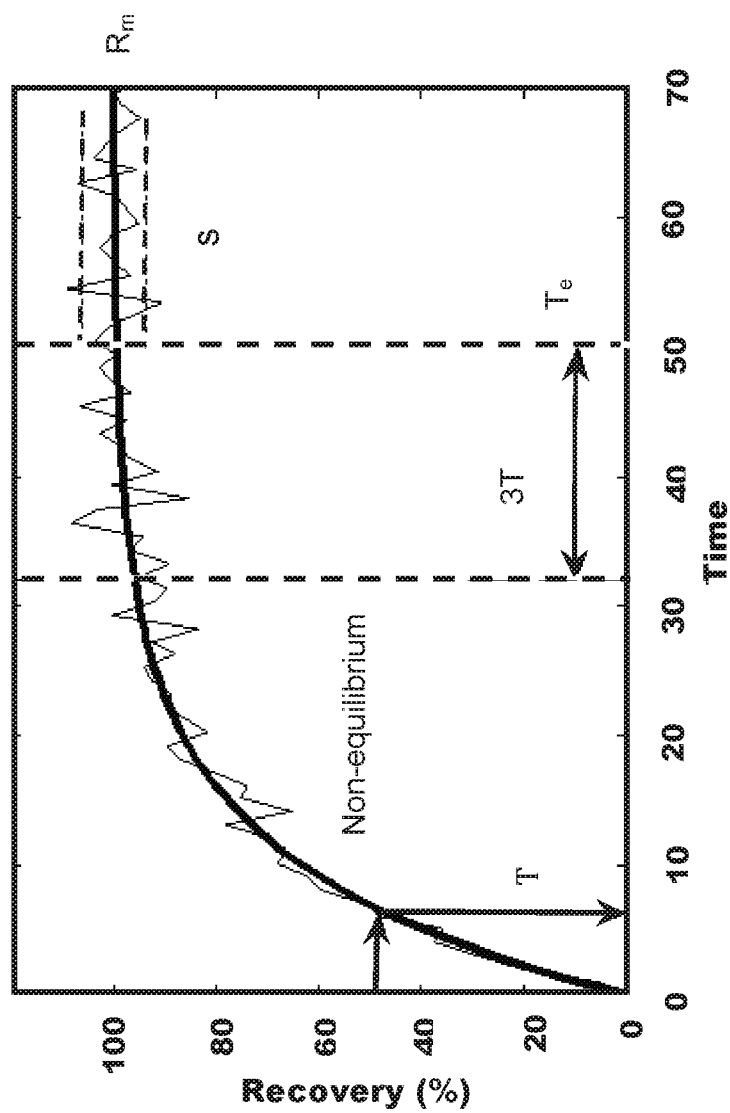
FIG. 8 shows a graphical illustration of the definition extraction equilibrium.

One operative definition of the time needed to reach equilibrium under a given set of conditions may be stated as follows (see also FIG. 8): $R_m$ is the maximum recovery obtained after very long extraction times, e.g. several hours, and S is the standard deviation of repeated measurements of recovery, R. Further, a characteristic time-scale for extraction, T, may be defined as the time taken for recovery, R, to reach half of $R_m$. The time, $T_e$, needed to reach equilibrium may then be defined as the time when the measured recovery, R, has changed less than one standard deviation, S, within a predetermined period greater than the characteristic time-scale, T (3*T, say). A definition of when the extraction has not reached equilibrium may be times earlier than this predetermined period (3*T, say) from equilibrium.

It is to be understood that 'substantially'; 'substantially similar' and like terms as used herein are to be taken to include any procedure employed in respect of an unknown sample matrices that varies from the ones employed at steps 110 and 120 in respect of the reference sample matrices to an extent that does not measurably impact the amount of analyte which would be extracted into the solvent from a same reference matrix.

Experimental Studies

The samples used in the demonstration of effects of different extraction times and solvent types consisted of a wheat sample matrix having reference mycotoxin levels of: DON: 1987 ppb±123 ppb and OTA: 18 ppb±3 ppb.

The samples used in the demonstration of extraction with 30% ethanol in 2 minutes consisted of five wheat sample matrices, each having a different mycotoxin concentration as per the table below:

| Mycotoxin Concentrations | | | |
|---|---|---|---|
| OTA | | DON | |
| Conc. [ppb] | ± [ppb] | Conc. [ppb] | ± [ppb] |
| <1 | | ND | |
| 4.3 | 1.1 | 900 | 100 |
| 21.5 | 5.8 | 1400 | 100 |
| 54.2 | 15.1 | 2100 | 200 |
| 101.8 | 12.2 | 3500 | 300 |

The used extraction solvents were aqueous solutions of ethanol (30% V/V), acetonitrile (60% V/V) and methanol (80% V/V). The choice of the organic component of the solvent was based what normally is used in scientific studies.

Extraction times of 1, 2, 4 and 30 min. were chosen. The 30 minutes extraction times were used as a reference and a measure of the maximum recovery, $R_m$, of each extraction solvent. In order to obtain precise extractions, a fast separation was performed by filtering in a French press before a fine filtering. The French press is similar in construction and operation to the well known French coffee press and comprises a narrow cylindrical beaker equipped with plunger that fits tightly but slidably in the cylinder and which has a mesh filter at one end. As the plunger is moved through the mixture consisting of sample matrix and analyte containing solvent the solvent is forced through the filter and separated from the sample matrix. This pressure enhanced separation increased the speed from extraction to separated extract greatly, and it normally took no longer that 30 seconds. In an alternative embodiment the extraction may be performed using a standard centrifuge to separate the solvent and the sample matrix, for example by means of filtration or sedimentation.

Figure 2:
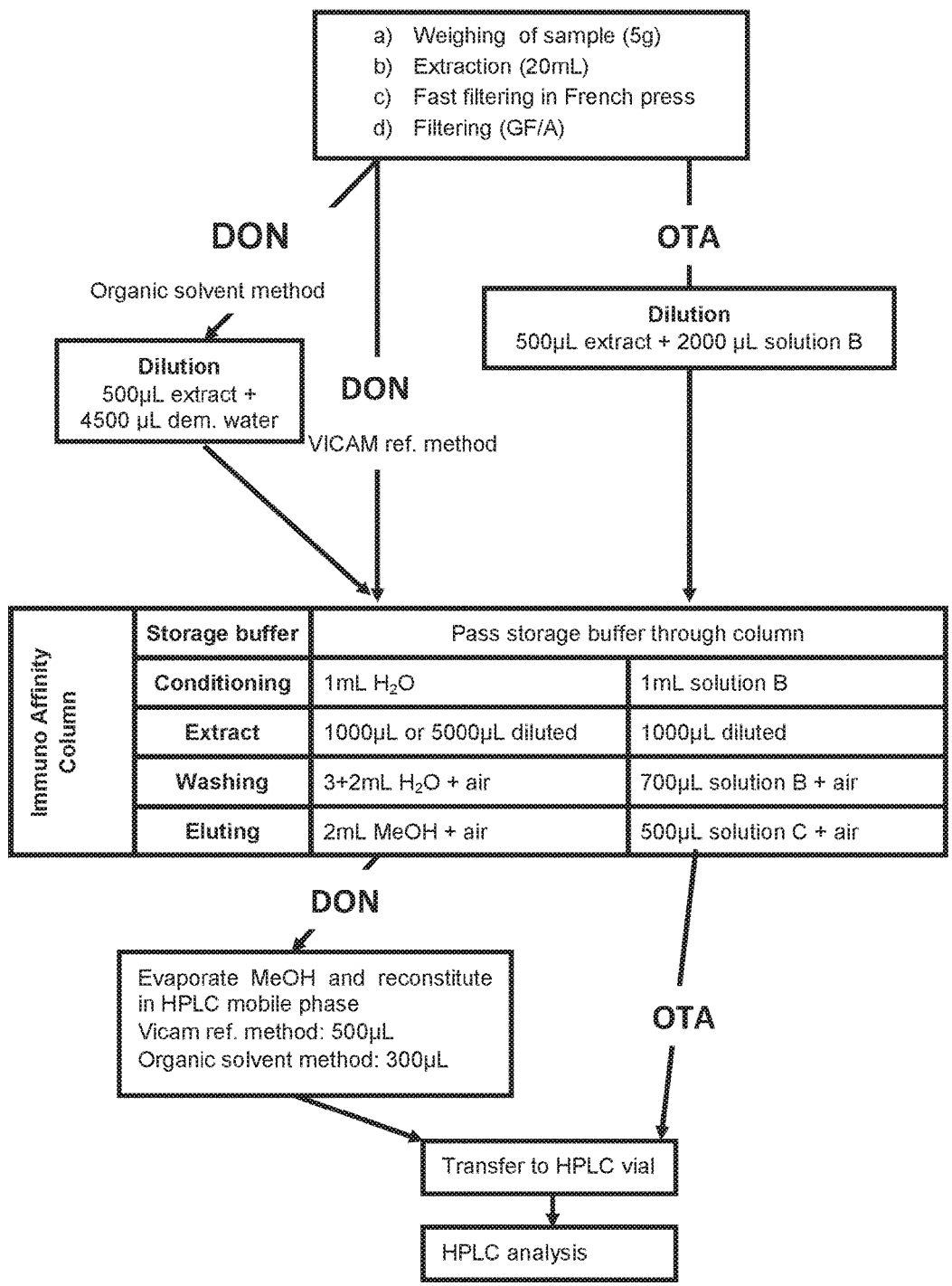
FIG. 2 shows a flow diagram illustrating a second embodiment of the method according to the present invention and employed in the experimental studies.

An overview of the extraction and sample clean up procedures for DON and OTA in connection with HPLC analysis in a method according to the present invention which is employed in the experimental studies is illustrated in FIG. 2.

In the sample preparation of DON for the reference method of a VICAM DONtest WB immuno affinity column (IAC) was used as a clean-up step. The reference method follows the procedure for sample preparation described by VICAM (DONtest HPLC & DONtest WB, Instruction Manual (for HPLC use), Rev. B, VICAM). HPLC settings used were: 1 mL/min flow of acetonitrile/water 10/90. 50 µL injected with 500 µL/min draw and inject speed. Column: Phenomenex reverse phase Synergi 4 µm, Hydro-RP 250× 4.6 mm, with precolumn. Column department heated to 30° C. UV-VIS detection at 218 nm±2 nm with reference at 500 nm±50 nm.

The extraction and clean up procedure followed is:
1. Sample 5 g of fine ground wheat (step 210a)
2. Extract with 20 mL of dem. water, while stirring the mixture in a sealed container. (step 210b))
3. Fast filter in French press and sample 5 mL of the liquid phase (use syringe). (step 210c))
4. Filter through a Whatman GF/A filter. The filtrate must be clear (OD600<0.02). (step 210d))
5. Let IAC temperate to ambient temperature (5 min.)
6. Pass storage buffer through the IAC. (step 220)
7. Wash the IAC with 1 mL dem. water.
8. Add 1 mL filtered extract to the IAC and let it pass through with approx. 1 drip/sec.
9. Wash the IAC with 5 mL dem. water (1 drip/sec.). Apply air pressure until air comes through the column and blot the tip with paper.
10. Elute with 2 mL of methanol in minimum 5 min (<1 drip/sec). Apply air pressure until air comes through the column.
11. Evaporate methanol from the sample and reconstitute with 500 µL HPLC mobile phase. (step 230)
12. Transfer to HPLC vial and make HPLC analysis. (step 240)

For quantification of DON extracted with organic solvents a dilution step (step 215a) is included in the sample preparation. This is because the VICAM IAC is optimized for water extracts. If an extract with a high content of organic solvent is applied to the column, DON will not be bound in the column and a low recovery is achieved. When extracting with organic solvents the dilution step comprises:

The filtered extract is diluted 10 fold with water: 500 µL extract+4500 µL dem. water (point 4a).
All of the diluted extract (5 mL) is applied to the IAC, let it pass through with 1 drip/sec. (replaces point 8 above).
Evaporate methanol from the sample and reconstitute with 300 µL HPLC mobile phase (replaces point 11 above).

| Solutions Used | | | | |
|---|---|---|---|---|
| Description | Component | Mole weight [g/mol] | Concentration | Measurement |
| HPLC mobile phase | | | | Total volume 100 mL (140 samples) |
| | Acetonitril | | 10% Vol. | 10 mL |
| | Dem. water | | 90% Vol. | 90 mL |

For the extraction and Clean up of OTA the procedure followed was:
1. Sample 5 g of homogenous ground wheat. (step 210a))
2. Extract in 1 min. with 20 mL of solution A while stirring the mixture in a sealed container. (step 210b))
3. Fast filter through French press and sample 5 mL of the liquid phase (use syringe). (step 210c))
4. Filter through a Whatman GF/A filter. The filtrate must be clear. (step 210d))
5. Sample 500 µL of the extract and dilute to 2.5 mL with solution B. (step 215b)
6. Let IAC temperate to ambient temperature (5 min.).
7. Pass storage buffer through the IAC. (step 220)
8. Wash the IAC with 1000 µL of solution B.
9. Add 1 mL diluted extract to the IAC, let it pass through with 1 drip/sec.
10. Wash the IAC with 700 µL of solution B (1 drip/sec.). Apply air pressure until air comes through the column and blot the tip with paper.
11. Elute with 500 µL of solution C (<1 drip/sec). Apply air pressure until air comes through the column.
12. Transfer to HPLC vial and make HPLC analysis. (step 240)

| Solutions Used | | | | |
|---|---|---|---|---|
| Description | Component | Mole weight [g/mol] | Concentration | Measurement |
| A | | | | Total volume 600 mL (30 samples) |
| | Acetonitrile | | 60% Vol. | 360 mL |
| | Dem. water | | 40% Vol. | 800 mL |
| B | | | | Total volume 1 L (250 samples) |
| | Tris | 121.14 | 12.5 mM | 1.5143 g |
| | NaCl | 58.44 | 150 mM | 8.7660 g |
| | KCl (Zero Liquid Salt P/N 1015912) | 74.55 | 6.25 mM | 0.4659 g |
| | MgCl (anhydrate) | 95.21 | 6.25 mM | 0.5951 g |
| | Dem. water | | | To 1 L |
| C | | | | Total volume 100 mL (140 samples) |
| | Acetonitrile | | 49.5% Vol. | 49.5 mL |
| | Dem. water | | 49.5% Vol. | 49.5 mL |
| | CH3COOH | | 1% Vol. | 1 mL |

Figure 3:
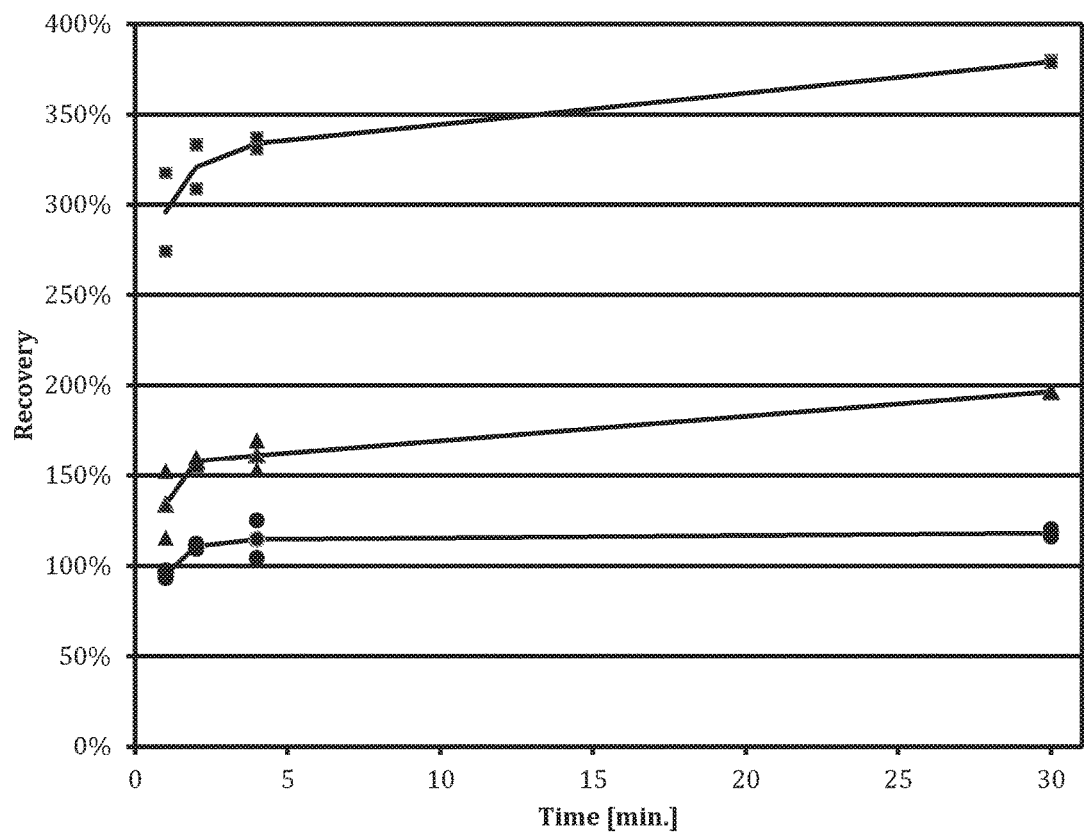
FIG. 3 shows time dependent recoveries of DON with different solvents.

Results from the experiment with varying extraction solvent and time using one naturally contaminated wheat sample (1987 ppb DON and 18 ppb OTA) are illustrated in FIG. 3.

In FIG. 3 plots of the recoveries for extraction of DON with 60% acetonitrile (triangle data set), 80% methanol (circle data set) and 30% ethanol (square data set) in water at different extraction times are illustrated. The recoveries are unusual high, which originates from sample clean-up problems. What can be deduced from FIG. 3 is that, for all three solvents, the highest gain of DON per minute happens in the first four minutes and that water content of the solvent seems to have a positive effect on the recovery.

Figure 4:
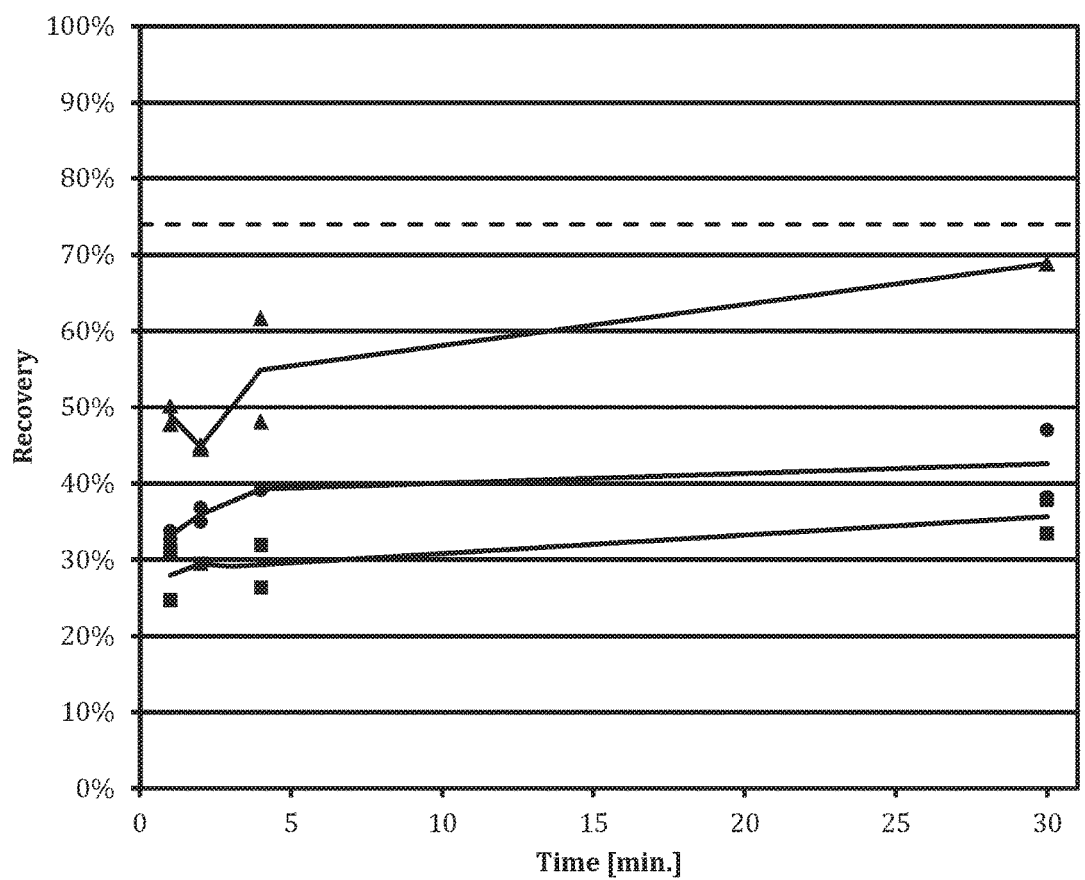
FIG. 4 shows time dependent recoveries of OTA with different solvents.

The same is evident when plotting the recoveries of OTA as a function of extraction time for different solvents; the largest amount of mycotoxin is extracted during the first four minutes (FIG. 4). The reference solvent for extraction is 60% acetonitrile (triangle data set) and gives a recovery of approximately 50% at the short extraction times, 30% ethanol (square data set) gives a recovery of approximately 30%, or 40% lower than 60% acetonitrile. 80% methanol (circle data set) gives recoveries in between 60% acetonitrile and 30% methanol. The lower limit of uncertainty for the reference value of OTA is illustrated by the dashed line and as can be seen, after 30 minutes the acetonitrile extraction is approaching this value.

Generally OTA extracted by 60% acetonitrile in 1-4 min gave recoveries from 45-55%. In the same interval 30% ethanol gave recoveries of 28-29%. 80% methanol gave recoveries in between with 33-39%. It can be deduced from the time and solvent experiments for DON that the largest amount of DON is extracted within the first 4 minutes and that the water content of the solvent has a positive effect on the recovery.

Figure 5:
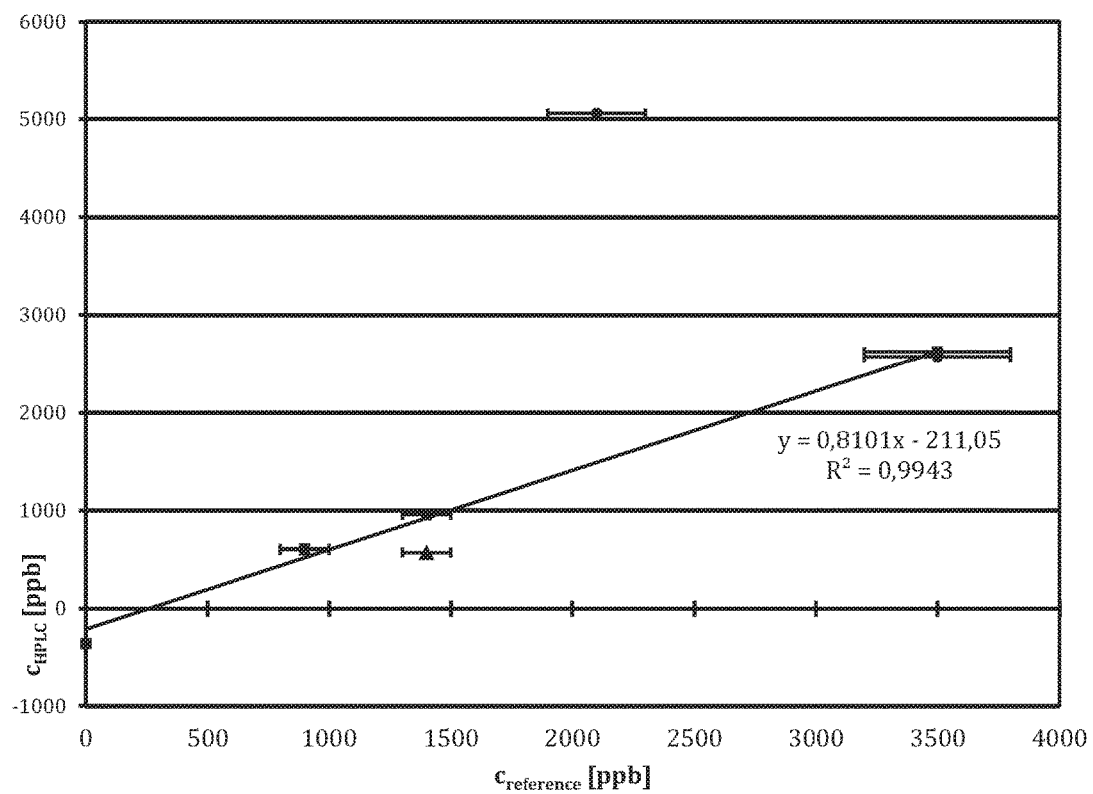
FIG. 5 shows the correlation between DON concentrations found by HPLC and reference concentrations.
Figure 6:
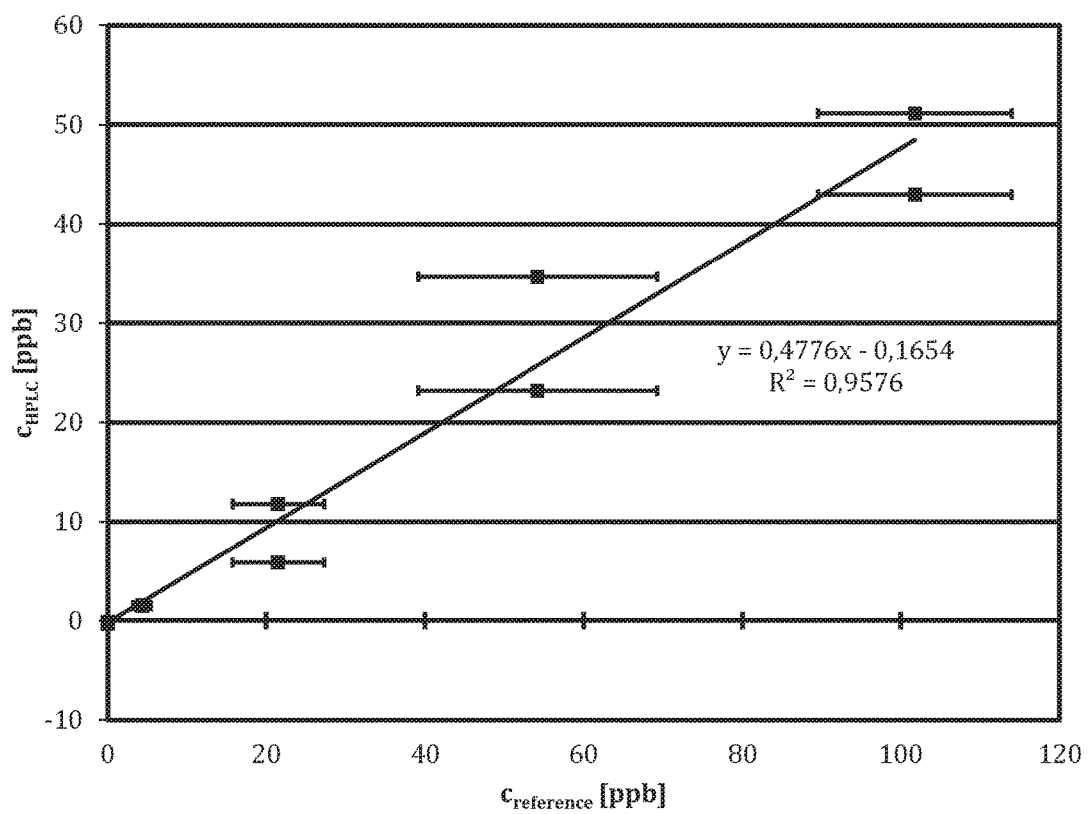
FIG. 6 shows the correlation between OTA concentrations found by HPLC and reference concentrations.

As demonstrated above it will be appreciated that 30% ethanol in water could be a feasible solvent for fast extraction of both DON and OTA, and is chosen for further experiments. Indeed a fast but incomplete extraction of both DON and OTA may be achieved using an ethanol concentration of between 20% and 40% in water. In FIG. 5 the correlation between DON concentrations found by HPLC and reference concentrations from 5 samples is plotted. One repetition is removed because of an extraction error (triangle); a lump of flour was discovered after extraction leading to a lower recovery of that sample. One other sample was an unexplained outlier (circle) and was excluded. A clear linear correlation is seen, with an average recovery of 70% and recovery CV of 5%. The corresponding plot for five different reference samples, having differing concentrations of OTA, is seen in FIG. 6. A linear correlation is also seen between the concentrations found by HPLC and reference values. The average recovery was 44% with a recovery CV of 27%. The high CV value could be because the extraction was done by three different people.

Linear regression analysis, here for example in the form of a least squares fit, was performed on the DON datasets and the OTA datasets and the resulting straight line fits are shown in FIG. 5 and FIG. 6 respectively.

As will be appreciated from a consideration of the above experimental studies a fast extraction method for mycotoxins, illustrated here for Deoxynivalenol (DON) and Ochratoxin A (OTA), has been established. It is possible to extract mycotoxins with 30% ethanol in 2 minutes with an average recovery of 70% for DON and 44% for OTA. For concentrations found by HPLC and reference concentrations, linear regressions could be obtained for the different mycotoxins, from which a computer executable calibration expressing each regression could be established for use in determining amounts of analytes in an unknown sample matrix (for example wheat) from levels present in solvent extracted using substantially similar techniques to those described above. For DON in the range of 0-3500 ppb a R-squared value of 0.99 was found, and for OTA in the range of 0-101.8 ppb the R-squared was 0.96.

It will be appreciated that the method according to the present invention is suitable for use in extracting other mycotoxins, such as fumonisins, ZEA, T2-toxin and aflatoxins, from the same or other types of cereal grains and may be applied more generally to other extraction based assays which traditionally rely on complete recovery. It is intended that the scope of protection afforded to the invention is limited only by the wording of the claims and not by the exemplary embodiments and experimental studies provided above.

The invention claimed is:

1. A method for a quantitative assay of one or more mycotoxins in a cereal grain sample matrix, the method comprising:
  performing solid-liquid analyte extraction of an analyte including the one or more mycotoxins on the cereal grain sample matrix, the cereal grain sample matrix including a solid-phase cereal grain sample representing a solid-phase cereal grain product, said solid-liquid analyte extraction including
    combining the cereal grain sample matrix with a solvent for a particular extraction period, the particular extraction period being less than a period of time associated with reaching equilibrium in an extraction process, and
    performing solvent separation to separate an instance of solvent from the cereal grain sample matrix, the instance of separated solvent containing at least a portion of the analyte;
  measuring a level of analyte present in the separated solvent; and
  applying a mathematical relationship between levels of analyte extracted from each reference cereal grain sample matrix of a plurality of reference cereal grain sample matrices, based on performing the solid-liquid analyte extraction and the measuring with regard to each reference cereal grain sample matrix of the plurality of reference cereal grain sample matrices, and corresponding reference values of the levels of analyte for each reference cereal grain sample matrix of the plurality of reference cereal grain sample matrices to determine a measure of the level of analyte in the cereal grain sample matrix, each reference cereal grain sample matrix including a solid-phase cereal grain reference sample representing the solid-phase cereal grain product:
  identifying a presence of the analyte in the solid-phase cereal grain product represented by the solid-phase cereal grain sample based on the determination; and
  designating the solid-phase cereal grain product for a separate analysis of levels of analyte presence in the solid-phase cereal grain product in response to the identifying.

2. The method as claimed in claim 1 wherein measuring the level of analyte includes
  mixing the instance of separated solvent with a particular amount of fluorescently labelled analyte molecules and with micro-beads having, at their surface, molecules having a preferential binding affinity for the analyte; and
  measuring fluorescence using a flow cytometer as the measure of the level of analyte, subsequently to performing the mixing.

3. The method as claimed in claim 2, wherein the mixing the instance of separated solvent includes incubating with the micro-beads for a particular period of time that is less than a period of time associated with establishing reaction equilibrium before measuring fluorescence.

4. The method as claimed in claim 1, wherein the mathematical relationship is generated based on
  performing solid-liquid analyte extraction on the plurality of reference cereal grain sample matrices, each reference cereal grain sample matrix of the plurality of reference cereal grain sample matrices associated with a different reference value level of the analyte, said analyte extraction including performing, for each reference cereal grain sample matrix, combining the reference cereal grain sample matrix with a solvent for the particular extraction period, and separating a separate instance of solvent from the reference cereal grain sample matrix, the instance of separated solvent containing at least a portion of the analyte;

measuring a level of the analyte present in the instances of separated solvent obtained from each reference cereal grain sample matrix; and determining the mathematical relationship as a relationship between measured levels of analyte present in the instances of separated solvent separated from the reference cereal grain sample matrices and corresponding different reference value levels of the analyte associated with the reference cereal grain sample matrices.

5. A method for a quantitative assay of one or more mycotoxins in a cereal grain sample matrix, the method comprising:

performing solid-liquid analyte extraction of an analyte including the one or more mycotoxins on a plurality of reference cereal grain sample matrices, each reference cereal grain sample matrix of the plurality of reference cereal grain sample matrices including a solid-phase cereal grain reference sample representing a solid-phase cereal grain product, each reference sample matrix associated with a different reference value level of the analyte, said solid-liquid analyte extraction including performing, for each reference cereal grain sample matrix, combining the reference cereal grain sample matrix with a solvent for a particular extraction period, the particular extraction period being less than a period of time associated with reaching equilibrium in an extraction process, and performing solvent separation to separate an instance of solvent from the reference cereal grain sample matrix, the instance of separated solvent containing at least a portion of the analyte;

measuring a level of the analyte present in the instance of separated solvent obtained from each reference cereal grain sample matrix;

determining a mathematical relationship between measured levels of analyte present in the instances of separated solvent separated from the reference cereal grain sample matrices and corresponding different reference value levels of the analyte associated with the reference cereal grain sample matrices, respectively;

combining an unknown cereal grain sample matrix with the solvent for the particular extraction period, the unknown cereal grain sample matrix including a solid-phase cereal grain sample representing the solid-phase cereal grain product, performing solid-liquid solvent separation to separate a separate instance of solvent from the unknown cereal grain sample matrix, and measuring a level of the analyte present in the instance of separated solvent obtained from the unknown cereal grain sample matrix, the unknown cereal grain sample matrix including an unknown level of the analyte, the instance of separated solvent containing at least a portion of the unknown level of the analyte;

applying the mathematical relationship to level of the analyte present in the instance of separated solvent obtained from the unknown cereal grain sample matrix to determine the unknown level of the analyte in the unknown cereal grain sample matrix;

identifying a presence of the analyte in the solid-phase cereal grain product represented by the solid-phase cereal grain sample based on the determination; and designating the solid-phase cereal grain product for a separate analysis of levels of analyte presence in the solid-phase cereal grain product in response to the identifying.

6. The method as claimed in claim 5, wherein each particular solvent separation includes separating a particular solvent from a particular cereal grain sample matrix under an applied force.

7. The method as claimed in claim 5, wherein the one or more mycotoxins are at least one of Deoxyrsivalenol (DON) and Ochratoxin A (OTA).

8. The method as claimed in claim 7, wherein the solvent is an alcohol:water mixture containing between 20% and 40% ethanol by volume.

9. The method as claimed in claim 8, wherein the solvent contains 30% ethanol by volume.

10. The method as claimed in claim 5, wherein the determining the mathematical relationship includes performing a linear regression analysis to establish the mathematical relationship.

11. The method as claimed in claim 5, wherein the measuring levels of the analyte present in the instances of separated solvent includes, for each instance of separated solvent, mixing the instance of separated solvent with a particular amount of fluorescently labelled analyte molecules and with micro-beads having, at their respective surfaces, molecules having a preferential binding affinity for the analyte; and measuring fluorescence using a flow cytometer as a measure of the level of analyte, subsequently to performing the mixing.

12. The method as claimed in claim 11, wherein the mixing is performed for a particular period of time that is less than a period of time associated with to establishing reaction equilibrium before measuring the fluorescence.

13. The method as claimed in claim 5, wherein the particular extraction period is a period of time associated with solvent extraction of one-half of a maximum amount of the analyte that can be extracted by the solvent, the period of time associated with reaching equilibrium in the extraction process is a period of time associated with a measured recovery of analyte that is associated with a deviation of repeated measurements of extracted analyte that is less than one standard deviation over a particular segment of elapsed time.

14. The method as claimed in claim 13, wherein the particular extraction period is one-third of a magnitude of the period of time associated with reaching equilibrium in the extraction process.

* * * * *